United States Patent [19]

Everly

[11] 4,451,676

[45] May 29, 1984

[54] CHEMICAL PROCESS FOR THE PREPARATION OF PARA-ALKENYL PHENOL

[75] Inventor: Charles R. Everly, Baton Rouge, La.

[73] Assignee: Ethyl Corporation, Richmond, Va.

[21] Appl. No.: 412,151

[22] Filed: Aug. 27, 1982

[51] Int. Cl.³ ............................................. C07C 39/18
[52] U.S. Cl. .................................. 568/780; 568/781; 568/790
[58] Field of Search ........................ 568/780, 781, 790

[56] References Cited

U.S. PATENT DOCUMENTS

| | | | |
|---|---|---|---|
| 2,194,215 | 3/1940 | Brunson et al. | 568/780 |
| 3,413,347 | 11/1968 | Worrel | 568/780 |
| 3,592,951 | 7/1971 | Zaweski | 568/780 |
| 3,725,480 | 4/1973 | Thornton et al. | 568/780 |
| 4,215,229 | 7/1980 | Greco | 568/780 |

FOREIGN PATENT DOCUMENTS 2363464 10/1981 Fed. Rep. of Germany ...... 568/780

Primary Examiner—Werren B. Lone
Attorney, Agent, or Firm—Donald L. Johnson; John F. Sieberth; W. G. Montgomery

[57] ABSTRACT p-Alkenyl phenols are prepared by reacting an alkylated phenol having a replaceable hydrogen atom at the 4- position with an aliphatic aldehyde having two carbon atoms up to at least 20 carbon atoms in the molecule and a secondary amine.

18 Claims, No Drawings

CHEMICAL PROCESS FOR THE PREPARATION OF PARA-ALKENYL PHENOL

TECHNICAL FIELD

This invention relates to a novel process for the preparation of p-alkenyl phenols. More particularly, this invention relates to a novel process for the preparation of 1,1-hydrocarbyl-substituted-2-(3'-hydrocarbyl or 3',5'-dihydrocarbyl-4'-hydroxyphenyl)ethene compounds which are especially useful as intermediates in the preparation of phenolic antioxidants for gasoline, lubricants, plastics and rubber.

THE INVENTION

In accordance with the invention, an alkylated phenol having a replaceable hydrogen atom at the 4-position and at least one hydrocarbyl substituent ortho to the hydroxyl group is reacted with an aliphatic aldehyde having two carbon atoms up to at least 20 carbon atoms in the molecule and a secondary amine to form the corresponding 1,1-hydrocarbyl-substituted-2-(3'-hydrocarbyl or 3',5'-dihydrocarbyl-4'-hydroxyphenyl)ethene.

The invention can best be understood by the following detailed discussion of the reactants and conditions by which the p-alkenyl phenol products of the present process are produced. The structure of these products will, of course, be determined by the nature of the starting phenolic and aldehyde reactants.

In general, any monohydroxybenzene compound having a replaceable hydrogen atom on the ring carbon atom para to the hydroxyl substituent and at least one hydrocarbyl substituent ortho to the hydroxyl group, as in the case of o-tert-butyl phenol, will serve as the starting phenol. Since the products of the process are principally useful as antioxidants or as intermediates in the preparation of antioxidants, it is desirable that the hydrocarbyl substituents be alkyl, aralkyl or cycloalkyl groups sufficiently large to offer some degree of hindrance to the phenolic group. It is especially desirable that the hydrocarbyl substituent be branched on the alpha-carbon atom and have at least 3 carbon atoms and, preferably, up to 8 carbon atoms; although any number of carbon atoms, for example up to about 40 carbon atoms, may be present in the hydrocarbyl substituent as long as the substituents do not interfere with the formation of the desired phenolic styrene. Suitable o-hydrocarbyl phenols meeting these requirements include secondary alkyl-substituted phenols such as o-isopropyl phenol, o-sec-butyl phenol, o-sec-amyl phenol and o-cyclohexyl phenol; while suitable tertiary hydrocarbyl phenols are o-tert-butyl phenol and o-tert-amyl phenol. Additionally, primary hydrocarbyl phenols, such as o-benzylphenol, can serve as starting phenols.

Most preferred phenolic reactants in the process of this invention are dialkyl phenols wherein the phenol has a replaceable hydrogen atom on the para ring carbon atom and two hydrocarbyl substituents ortho to the hydroxyl group. Preferably, at least one of the hydrocarbyl substituents is branched on the alpha-carbon atom and has from 3 to 8 carbon atoms. The substituents need not both be the same hydrocarbyl radical. Specific examples of particularly appropriate phenols are represented by 2,6-dimethyl phenol, 2,6-di-n-butyl phenol, 2,6-di-sec-butyl phenol, 2-isopropyl-6-methyl phenol, 2,6-diisopropyl phenol, 2,6-di-tert-butyl phenol, 2,6-di-sec-octyl phenol, 2-methyl-6-cyclohexyl phenol, 2,6-di-(α-methylbenzyl)phenol, 2,6-dibenzyl phenol, 2-methyl-6-benzyl phenol and the like. A particularly preferred phenolic reactant for use in the present process is 2,6-di-tert-butyl phenol.

Substituent groups other than those previously listed such as aryl, chlorine, bromine, fluorine and nitro groups and the like may be present at any of the ring carbon atoms with the sole exception of the para ring carbon atom in the aromatic phenolic reactant provided they do not adversely affect the formation of the desired 1,1-hydrocarbyl-substituted-2-(3'-hydrocarbyl or 3',5'-dihydrocarbyl-4'-hydroxyphenyl)ethene product.

Preferred starting phenolic reactants may be described by the structure

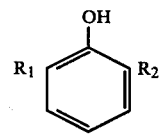

wherein $R_1$ and $R_2$ are the same or different and are hydrogen or hydrocarbyl radicals, preferably alkyl, aralkyl or cycloalkyl radicals having up to at least 40 carbon atoms, and preferably from 3 to 8 carbon atoms, at least one of which is branched on the alpha-carbon atom with the provision that at least one of $R_1$ or $R_2$ must be other than hydrogen.

Aldehydes which are applicable to the present process are those aldehydes having a single aldehyde radical of the general formula

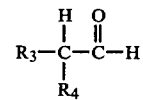

wherein $R_3$ and $R_4$ can be the same or different and are selected from hydrogen or linear and branched alkyl radicals having up to at least 40 carbon atoms, preferably up to 20 carbon atoms. Typical aldehydes which may be used in the process of the invention include, by way of example only acetaldehyde, propionaldehyde, butyraldehyde, isobutyraldehyde, caprylaldehyde, decylaldehyde, tetradecylaldehyde, and the like.

Amine reactants which are applicable to the present process are secondary amines; that is, derivatives of ammonia having one hydrogen atom bonded to the amino nitrogen atom and can be represented by the formula

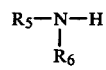

wherein $R_5$ and $R_6$ are the same or different and are linear or branched alkyl radicals having up to at least 40 carbon atoms. It is deemed, however, that secondary amines containing nitrogen atoms in a ring structure such as piperidine, pyrrolidine, morpholine and the like also may be used. Preferred amines are dimethylamine, diethylamine, dipropylamine, dibutylamine, disecondarypropylamine, ethylmethylamine, methylpropylamine, methyl-n-butylamine, ethylisopropylamine and the like.

Under the reaction conditions, the amino reactant initially combines with the phenolic and aldehyde reactants to yield a Mannich base type of intermediate which upon further reaction spontaneously eliminates the amine component to produce the olefinic final product. The carbonyl carbon atom of the aldehyde reactant, along with the organic groups bonded to the carbonyl carbon atom of the aldehyde, becomes bonded to the 4-carbon atom of the phenol ring. Some aldol condensation by-product is produced during the reaction. The overall reaction is shown in the following schematic diagram:

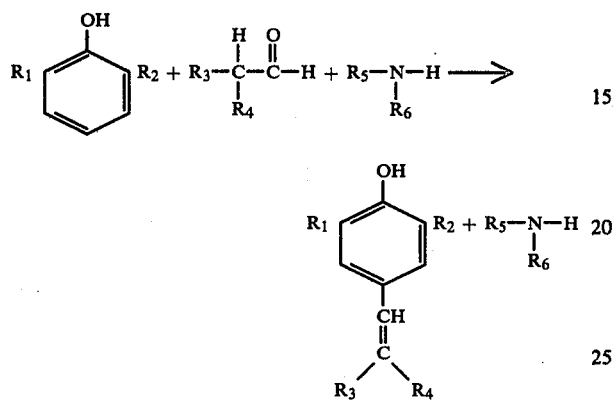

wherein $R_1$, $R_2$, $R_3$, $R_4$, $R_5$ and $R_6$ are as previously defined.

The process of the invention is carried out by reacting the phenolic starting material with at least one molar equivalent of aldehyde and at least 0.1 molar equivalent of amine. It is preferred, however, that the reaction be conducted with a molar excess of both aldehyde and amine reactants with respect to the starting phenol. A preferred range of aldehyde to phenolic reactant is from about 1 to 10 moles of aldehyde per mole of phenol. A preferred molar range of amine reactant to phenolic reactant is from about 0.1 to 10 moles of amine per mole of phenol.

The reaction can be conducted at a temperature from about 50° C. to about 250° C. While lower temperatures can be used, the reaction rates are generally too low to be of interest. Temperatures above 250° C. can be used, but excessive decomposition of the reaction components can occur. The preferred reaction temperatures are from about 50° C. to about 200° C.

The reaction can be conducted at atmospheric pressure or at higher pressures, with moderate pressures up to about 300 psig being preferred.

The use of a solvent for the reaction mixture is not generally required, though, if desired, a solvent which is inert under the reaction conditions, i.e., those solvents which do not enter into the reaction, may be added to the reaction vessel. Useful solvents comprise aprotic solvents which include ethers such as diethyl ether, dibutyl ether, 1-ethoxyhexane, tetrahydrofuran, 1,4-dioxane, 1,3-dioxolane, diglyme, 1,2-diethoxyethane and tertiary amines such as pyridine, N-ethylpiperidine, triethylamine, tributylamine, N,N-diphenyl-N-methyl amine, N,N-dimethylalanine, etc. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc. Especially preferred solvents are lower alkanols having up to about 6 carbon atoms. These include methanol, ethanol, n-propanol, isopropyl alcohol, n-butanol, sec-butyl alcohol, tert-butyl alcohol, n-pentanol, isopentyl alcohol, n-hexanol and isohexyl alcohol.

The amount of solvent can be expressed as a volume ratio of solvent to phenolic reactant. Suitable volume ratios of solvent to phenolic reactant can be from about 0/1 to about 500/1 and preferably from about 1/1 to about 300/1.

The mode of addition in the process is not particularly critical. Accordingly, it is convenient to add the phenolic reactant to a mixture of the other materials, add the aldehyde to a mixture of the other materials, add the amine reactant to a mixture of the other materials, add the reactants to a mixture of the amine and solvent, introduce all ingredients simultaneously into the reaction zone, or the like.

If a gaseous amine is selected for use in the process, the reaction is carried out by passing the amine in its gaseous state through the reaction mixture in a reaction vessel with agitation to obtain intimate contact of the reactants. To ensure that the amount of amine does not exceed that amount required, as hereinabove shown, the amount of amine in contact with the other reactants can be controlled by limiting the flow of amine through or into the reaction vessel.

The process should be carried out for the time sufficient to convert substantially all of the phenolic reactant to the corresponding p-alkenyl phenol. The length of time for optimum yield will depend primarily upon the reaction temperature and the particular solvent, if any, used in the reaction. In general, excellent yields of p-alkenyl phenol are obtained in from about two to forty-eight hours.

Although not required, the process can be conducted in a substantially anhydrous reaction system, and accordingly, the components of the reaction system are brought together and maintained under a substantially dry, inert atmosphere. By "substantially anhydrous" is meant a reaction system wherein the total amount of water present is no more than about 5 percent by weight, based on the reaction mixture. When the amount of water in the system exceeds this, both reaction rate and yield of product decrease.

The process may readily be conducted in a batchwise, semibatch or continuous manner and in conventional equipment.

The product p-alkenyl phenol is easily separated from the reaction mixture by such means as distillation, extraction crystallization and other methods obvious to those skilled in the chemical processing art.

The practice of this invention will be still further apparent by the following illustrative examples.

EXAMPLE I

Preparation of
1,1-Dimethyl-2-(3',5'-Di-t-Butyl-4'-Hydroxyphenyl)Ethene 2,6-di-tertiary-butyl phenol (4.1 g; 20 mmol), isobutyraldehyde (3 ml; 33 mmol), dimethylamine (1.5 g; 34 mmol) dissolved in isopropanol (7.5 g) were charged to a 100 ml glass vessel and refluxed at ambient pressure under nitrogen for 48 hours. The resultant reaction mixture was allowed to cool to ambient temperature and concentrated to a yellow oil which was recrystallized from a mixture of ethanol and water (90:10) to give yellow crystals (3.7 g; 71% yield) of 1,1-dimethyl-2-(3′,5′-di-t-butyl-4′-hydroxyphenyl)ethene as characterized by VPC, mass spectroscopy and NMR.

In a manner similar to Example I above, a number of experiments were carried out varying the temperature, reaction time, pressure, reactants and ratio of reactants. The results were analyzed by vapor phase chromotography with internal standards and are shown in the Table below.

TABLE

Preparation of 1,1-Dimethyl-4-(3′,5′-Di-t-Butyl-4′-Hydroxyphenyl)Ethene

| Run No. | 2,6-Di-t-butyl phenol (mmoles) | Isobutyraldehyde (mmoles) | Dimethylamine (mmoles) | Solvent (g.) | Temp. (°C.) | Pressure (psig) | Time (hr.) | % Yield |
|---|---|---|---|---|---|---|---|---|
| 2 | 40 | 45 | 45 | Isopropyl Alcohol - 12 | Reflux | Ambient | 12 | 5 |
| 3 | 20 | 33 | 34 | Isopropyl Alochol - 9 | Reflux | Ambient | 48 | 71 |
| 4 | 20 | 30 | 44 | Isopropyl Alcohol - 20 | 135-140 | ~25 | 5 | 20 |
| 5 | 20 | 30 | 37 | Toluene - 21 | Reflux | Ambient | 12 | No Reaction |
| 6 | 20 | 30 | 32 | Methanol - 21 | Reflux | Ambient | 2 | 3 |
| 7 | 20 | 30 | 76 | Acetone - 20 | Reflux | Ambient | 12 | 3 |
| 8 | 50 | 75 | 5 | Isopropyl Alcohol - 8 | 150-155 | ~50 | 2 | 6 |
| 9 | 25 | 37 | 53 | Neat | 100 | Ambient | 2 | 31 |
| 10 | 25 | 37 | 13 | Dimethylformamide - 15 | 120-130 | Ambient | 5 | 22 |
| 11 | 10 | 15 | 15 | Methanol - 5 | Reflux | Ambient | 12 | 6 |
| 12 | 25 | 37 | 37 | Methanol - 37 | 135-140 | ~25 | 1.5 | 10 |
| 13 | 40 | 42 | 42 | Dimethylformamide - 8.24 | 155 | 50 | 2.0 | 89 |
| 14 | 40 | 42 | 40 | Neat | 200 | 125 | 2.5 | 82 |

Preparation of 1-Butyl-2-(3,5-Di-t-Butyl-4′-Hydroxyphenyl)Ethene

| Run No. | 2,6-Di-t-butyl phenol (mmoles) | Hexanal (mmoles) | Dimethylamine (mmoles) | Solvent (g.) | Temp. (°C.) | Pressure (psig) | Time (hr.) | % Yield |
|---|---|---|---|---|---|---|---|---|
| 15 | 20 | 20 | 23 | Isopropanol - 6 | Reflux | Ambient | 72 | 45 |

Preparation of 1-Phenyl-2-(3,5-Di-t-Butyl-4′-Hydroxyphenyl)Ethene

| Run No. | 2,6-Di-t-butyl phenol (mmoles) | Phenylacetaldehyde (mmoles) | Dimethylamine (mmoles) | Solvent (g.) | Temp. (°C.) | Pressure (psig) | Time (hr.) | % Yield |
|---|---|---|---|---|---|---|---|---|
| 16 | 40 | 40 | 45 | Isopropanol - 12 | Reflux | Ambient | 72 | 2 |

Preparation of 4-Ethenyl-2,6-Di-t-Butyl-4′-Hydroxyphenol

| Run No. | 2,6-Di-t-butyl phenol (mmoles) | Acetaldehyde (mmoles) | Dimethylamine (mmoles) | Solvent (g.) | Temp. (°C.) | Pressure (psig) | Time (hr.) | % Yield |
|---|---|---|---|---|---|---|---|---|
| 17 | 40 | 160 | 136 | Isopropanol - 36 | ~100 | 25 | 16 | trace |

Preparation of Cis and Trans-1-Ethyl-2-(3,5-Di-t-Butyl-4′-Hydroxyphenyl)Ethene

| Run No. | 2,6-Di-t-butyl phenol (mmoles) | Butyraldehyde (mmoles) | Dimethylamine (mmoles) | Solvent (g.) | Temp. (°C.) | Pressure (psig) | Time (hr.) | % Yield |
|---|---|---|---|---|---|---|---|---|
| 18 | 40 | 40 | 42 | Neat | ~130 | 25 | 2.5 | 66 |

I claim:

1. A process for preparing a para-alkenyl phenol which comprises reacting at a temperature of from about 50° C. to about 250° C. an alkylated phenol having a replaceable hydrogen atom at the 4-position and at least one hydrocarbyl substituent ortho to the hydroxy group with an aliphatic aldehyde having from 2 carbon atoms up to at least 20 carbon atoms in the molecule and a secondary amine and separating the para-alkenyl phenol from the reaction mixture.

2. A process for preparing a 1,1-hydrocarbyl-substituted-2-(3′-hydrocarbyl or 3′,5′-dihydrocarbyl-4′-hydroxyphenyl)ethene which comprises reacting at a temperature of from about 50° C. to about 250° C. an alkylated phenol having a replaceable hydrogen atom at the 4-position and at least one hydrocarbyl substituent ortho to the hydroxy group with an aliphatic aldehyde having from 2 carbon atoms up to at least 20 carbon atoms in the molecule and a secondary amine and separating the 1,1-hydrocarbyl-substituted-2-(3′-hydrocarbyl or 3′,5′-dihydrocarbyl-4′-hydroxyphenyl)ethene from the reaction mixture.

3. A process for preparing 1,1-hydrocarbyl-substituted-2-(3′-hydrocarbyl or 3′,5′-dihydrocarbyl-4′-hydroxyphenyl)ethene which comprises reacting at a temperature of from about 50° C. to about 250° C. an alkylated phenol having the formula

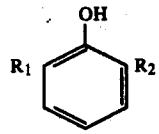

wherein $R_1$ and $R_2$ are the same or different and are hydrogen or hydrocarbyl radicals selected from the group consisting of alkyl, aralkyl or cycloalkyl radicals having up to at least 40 carbon atoms with the provision that at least one of the $R_1$ or $R_2$ radicals must be other than hydrogen with an aliphatic aldehyde having from 2 carbon atoms up to at least 20 carbon atoms in the molecule and a secondary amine and separating the 1,1-hydrocarbyl-substituted-2-(3′-hydrocarbyl or 3′,5′-dihydrocarbyl-4′-hydroxyphenyl)ethene from the reaction mixture.

4. A process for preparing 1,1-hydrocarbyl-substituted-2-(3′-hydrocarbyl or 3′,5′-dihydrocarbyl-4′-hydroxyphenyl)ethene which comprises reacting at a temperature of from about 50° C. to about 250° C. an alkylated phenol having the formula

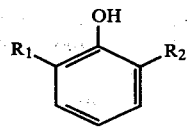

wherein $R_1$ and $R_2$ are the same or different and are hydrogen or hydrocarbyl radicals selected from the group consisting of alkyl, aralkyl or cycloalkyl radicals having up to at least 40 carbon atoms with the provision that at least one of the $R_1$ or $R_2$ radicals must be other than hydrogen with an aliphatic aldehyde having the formula

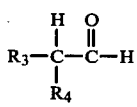

wherein $R_3$ and $R_4$ can be the same or different and are hydrogen or linear or branched alkyl radicals having up to at least 40 carbon atoms in the molecule with the provision that one of $R_3$ or $R_4$ must be other than hydrogen and a secondary amine having the formula

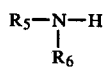

wherein $R_5$ and $R_6$ are the same or different and are linear or branched alkyl radicals having up to at least 40 carbon atoms and separating the corresponding 1,1-hydrocarbyl-substituted-2-(3'-hydrocarbyl or 3',5'-dihydrocarbyl-4'-hydroxyphenyl)ethene from the reaction mixture.

5. The process of claim 4 wherein the molar range of aldehyde to phenolic reactant is from about 1–10 moles of aldehyde per mole of phenol.

6. The process of claim 4 wherein the molar ratio of amine reactant to phenolic reactant is from about 0.1–10 moles of amine per mole of phenol.

7. The process of claim 4 wherein said aldehyde reactant is selected from acetaldehyde, propionaldehyde, butyraldehyde, isobutyraldehyde, caprylaldehyde, decylaldehyde and tetradecylaldehyde.

8. The process of claim 4 wherein said amine reactant is selected from dimethylamine, diethylamine, dipropylamine, dibutylamine, disecondarypropylamine, ethylmethylamine, methylpropylamine, methyl-n-butylamine and ethylisopropylamine.

9. The process of claim 4 wherein said reaction is carried out under pressure in the range of from about atmospheric up to about 300 psig.

10. The process of claim 4 wherein said reaction is carried out in the temperature range of from about 50° C. to about 250° C. and under pressure from the range of about atmospheric to about 300 psig.

11. The process of claim 4 wherein said reaction is carried out in the presence of a solvent which is inert under the reaction conditions.

12. The process of claim 11 wherein said solvent is an aprotic solvent.

13. The process of claim 12 wherein said aprotic solvent is a dipolar aprotic solvent.

14. The process of claim 13 wherein said dipolar aprotic solvent is selected from dimethyl sulfoxide, N,N-dimethylformamide, N,N-dimethylacetamide, dimethyl sulfone, tetramethylene sulfone, N-methylpyrrolidinone and acetonitrile.

15. The process of claim 11 wherein said solvent is selected from the group consisting of low boiling hydrocarbons, halogenated hydrocarbons and lower alkanols having up to about 6 carbon atoms.

16. The process of claim 11 wherein the volume ratio of solvent to phenolic reactant is from about 0.1/1 to about 500/1.

17. The process of claim 4 wherein the reaction is carried out under a substantially dry, inert atmosphere.

18. The process of claim 4 wherein the product is 1,1-dimethyl-2-(3',5'-di-t-butyl-4'-hydroxyphenyl)ethene, the phenolic reactant is 2,6-di-t-butylphenol, the aldehyde reactant is isobutyraldehyde and the amine reactant is dimethylamine.

* * * * *